*(12)* United States Patent
Friedberg

(10) Patent No.: US 9,050,090 B2
(45) Date of Patent: Jun. 9, 2015

(54) APPARATUS AND METHOD FOR FACILITATING ACCESS TO VESSELS

(75) Inventor: Joseph Friedberg, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 783 days.

(21) Appl. No.: 12/367,068

(22) Filed: Feb. 6, 2009

(65) Prior Publication Data

US 2009/0198259 A1   Aug. 6, 2009

Related U.S. Application Data

(60) Provisional application No. 61/026,603, filed on Feb. 6, 2008.

(51) Int. Cl.
*A61B 17/08* (2006.01)
*A61B 17/12* (2006.01)
*A61B 17/04* (2006.01)

(52) U.S. Cl.
CPC ....... *A61B 17/12013* (2013.01); *A61B 17/0483* (2013.01)

(58) Field of Classification Search
CPC ........... A61B 17/0401; A61B 17/0469; A61B 17/0482; A61B 17/0483; A61B 2017/0409; A61B 2017/0496; A61B 17/12013
USPC ......... 606/139, 151, 157, 158, 232, 205–211, 606/144–150; 600/37; 623/23.72
See application file for complete search history.

(56) References Cited

U.S. PATENT DOCUMENTS

| | | | | |
|---|---|---|---|---|
| 5,336,231 A | * | 8/1994 | Adair | 606/148 |
| 5,350,385 A | * | 9/1994 | Christy | 606/139 |
| 5,545,180 A | * | 8/1996 | Le et al. | 606/232 |
| 5,618,307 A | * | 4/1997 | Donlon et al. | 606/205 |
| 5,618,314 A | * | 4/1997 | Harwin et al. | 606/232 |
| 6,319,272 B1 | * | 11/2001 | Brenneman et al. | 606/232 |
| 7,601,159 B2 | * | 10/2009 | Ewers et al. | 606/139 |
| 2006/0271060 A1 | * | 11/2006 | Gordon | 606/103 |

* cited by examiner

*Primary Examiner* — Julian W Woo
(74) *Attorney, Agent, or Firm* — RatnerPrestia

(57) ABSTRACT

A device and method for facilitating access to a perimeter surface of a body structure is provided. The device includes an elongate flexible member configured to be positioned adjacent the perimeter surface of the body structure, an atraumatic tip positioned at a distal end of the elongate flexible member, and an elongate body. The elongate body has a surface positioned to guide the elongate flexible member and to permit longitudinal movement of the flexible member with respect to the elongate body. The body also has a curved distal portion and a distal end for releasably engaging the atraumatic tip.

10 Claims, 7 Drawing Sheets

APPARATUS AND METHOD FOR FACILITATING ACCESS TO VESSELS

CROSS REFERENCE TO RELATED APPLICATIONS

This application claims priority of U.S. Provisional Patent Application Ser. No. 61/026,603 filed Feb. 6, 2008, which is incorporated by reference herein in its entirety.

FIELD OF THE INVENTION

This invention relates to the field of surgical instruments, in particular, surgical instruments for accessing and controlling blood vessels or other tubular body structures such as the esophagus, bowel, ureters, nerves, and other body structures.

BACKGROUND OF THE INVENTION

The central dogma of all vascular surgical procedures is to obtain control of the blood vessel or other body structure upon which the surgeon is working. Control includes manipulation of a body structure. For example, it may include the ability to occlude a blood vessel, which often is accompanied by dissecting around the vessel, circumferentially, such that a clamp can be placed completely across it. The typical procedure for such blood vessel occlusion is to use a combination of sharp and blunt dissection to provide a region of the blood vessel under which a clamp can be placed. Once the vessel has been cleared 360 degrees of investing tissue, a clamp is placed behind the blood vessel and an elastic vessel loop is passed between the jaws of the clamp. The jaws are then closed and the clamp is withdrawn, thereby dragging the loop under the vessel. The loop may be placed 180 degrees around the circumference of the blood vessel and pulled upwards to elevate the portion of the blood vessel to be controlled. Alternatively, the loop may be encircled at least 360 degrees around the blood vessel and tensioned to control a portion of the vessel. Depending upon the integrity of the blood vessel being dissected, it may be safe to place the clamp under the blood vessel, before it is completely freed up posteriorly, and to oscillate the closed clamp back forth in an attempt to have the clamp bluntly define the posterior plane around the vessel.

Another technique is to place the clamp behind the blood vessel and to spread the tips, in an effort to perform controlled tearing of the tissue behind the vessel.

There is always some risk, with a metal instrument, of tearing the posterior wall of the blood vessel with either of these techniques, particularly the spreading technique as there is significant mechanical advantage rendered by the ratio of the length of the handle of the clamp compared to the length of the jaws. Regardless of the technique used to pass the clamp behind the vessel, the first time the clamp is closed to withdraw the loop, the back wall of the blood vessel or the investing tissue around the vessel can become caught in the jaws, along with the loop. This requires withdrawing and re-passing the clamp, which usually allows the loop to be grasped without trapping tissue. There is an element of risk associated with each passage of an instrument behind a blood vessel.

Once the loop is under the vessel it is considered "controlled" as the surgeon now has a means to either elevate the vessel loop and place a clamp under the vessel or to cinch down on the loop with a tourniquet, in either case restricting blood flow through the vessel. This standard procedure for controlling a blood vessel is, at best, tedious and often difficult and potentially risky.

Because of the challenges associated with accessing blood vessels or other body structures in procedures such as vascular surgery, there is a need for improved apparatus and methods for gaining access to a body structure such as a vessel. The present invention addresses this need, among others.

SUMMARY OF THE INVENTION

In one aspect, the invention provides a device that facilitates access to a perimeter surface of a body structure such as a vessel. The device includes an elongate flexible member configured to be positioned adjacent the perimeter surface of the body structure or vessel, an atraumatic tip positioned at a distal end of the elongate flexible member, and an elongate body. The elongate body has a surface positioned to guide the elongate flexible member and to permit longitudinal movement of the flexible member with respect to the elongate body. The body also has a curved distal portion and a distal end for releasably engaging the atraumatic tip.

In another aspect, a device is provided for impeding the flow of blood through a vessel. The device includes an elongate flexible member coupled to an atraumatic tip. The flexible member is configured to be positioned adjacent the perimeter surface of the vessel, and the tip has a surface configured to be grasped.

In yet another aspect, a method is provided for facilitating access to a perimeter surface of a vessel. The method includes positioning a curved distal portion of an elongate body of a device adjacent the perimeter surface of the vessel such that the perimeter surface of the vessel contacts a surface of the curved distal portion. An atraumatic tip positioned at a distal end of an elongate flexible member is grasped and moved longitudinally with respect to the curved distal portion so as to extract the flexible member from the curved distal portion of the elongate body. The elongate body is then at least partially withdrawn such that the elongate flexible member contacts the perimeter surface of the vessel.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Figure 1:
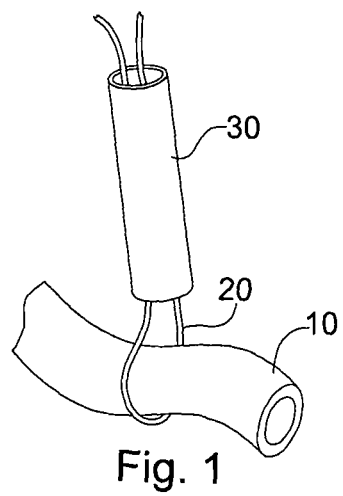
FIG. 1 is a perspective view of a method of clamping a vessel with a tourniquet and an elongate flexible member.

Although the invention is illustrated and described herein with reference to specific embodiments, the invention is not intended to be limited to the details shown. Rather, various modifications may be made in the details within the scope and range of equivalents of the claims and without departing from the invention.

Referring generally to the figures, in accordance with an exemplary embodiment, the invention provides a device 100, 200 that facilitates access to a perimeter surface of a body structure such as a vessel 10. The device 100, 200 includes an elongate flexible member 120 configured to be positioned adjacent the perimeter surface of the vessel 10, an atraumatic tip 130 positioned at a distal end of the elongate flexible member 120, and an elongate body 110. The elongate body 110 has a surface 144 positioned to guide the elongate flexible member 120 and to permit longitudinal movement of the flexible member 120 with respect to the elongate body 110. The body 110 also has a curved distal portion 2 and a distal end 3 for releasably engaging the atraumatic tip 130.

In a further embodiment of the present invention, a method for facilitating access to a perimeter surface of a vessel 10 is provided. The method includes positioning a curved distal portion 2 of an elongate body 110 of a device 100, 200 adjacent the perimeter surface of the vessel 10 such that the perimeter surface of the vessel 10 contacts a surface of the curved distal portion 2. An atraumatic tip 130 positioned at a distal end 3 of an elongate flexible member 120 is grasped and moved longitudinally with respect to the curved distal portion 2 so as to extract the flexible member 120 from the distal end 3 of the elongate body 110. The elongate body 110 is at least partially removed or retracted or withdrawn such that the elongate flexible member 120 contacts the perimeter surface of the vessel 10.

Referring now to the individual figures in detail, FIG. 1 illustrates a method for accessing and controlling a blood vessel 10. In the body, blood vessel 10 may be surrounded and attached to connective tissue which limits a surgeon's access to the perimeter surface of blood vessel 10. In order to isolate blood vessel 10, the surgeon may use his or her fingers to feel their way behind vessel 10 to safely separate blood vessel 10 from connective tissue. Blood vessel 10 may then be encircled by an elongate flexible member 20 such that a portion of flexible member 20 is used to form a loop around the perimeter surface of vessel 10. To control blood flow in vessel 10, a tourniquet 30 is passed over the ends of flexible member 20. Tourniquet 30 is cinched down, e.g., drawn towards the surface of vessel 10, such that the diameter of the loop decreases and firmly contacts vessel 10. Tourniquet 30 may then be clamped with a remote surgical clamp (not shown) to secure the position of tourniquet 30 and control blood flow through vessel 10.

Figure 2:
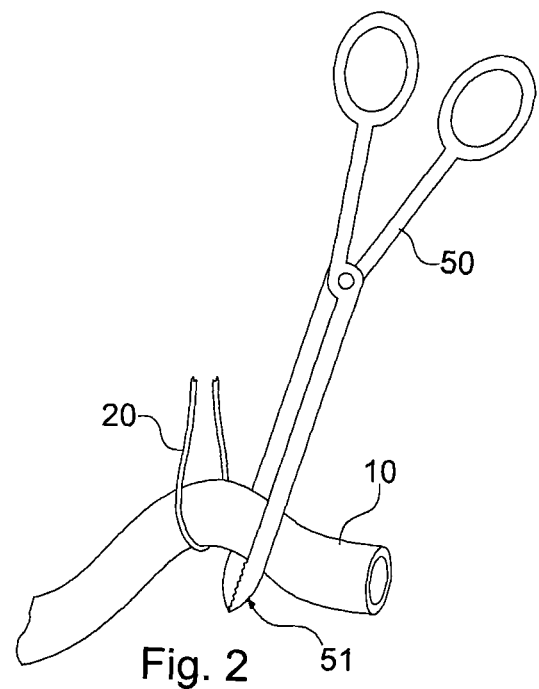
FIG. 2 is a perspective view of a method of elevating and clamping a vessel with a surgical clamp.

In another method illustrated in FIG. 2, a clamp 50 is placed across blood vessel 10 and an elongate flexible member 20, such as a vessel loop, is used to elevate blood vessel 10 in an inverted-V configuration so that one jaw of clamp 50 can be placed under blood vessel 10 and clamp the blood vessel 10. As shown in FIG. 2, the loop 20 is placed 180 degrees around the circumference of the blood vessel 10 and ends of the loop may be pulled upwards to elevate the blood vessel 10. Alternatively, the loop 20 may be encircled in a double loop (e.g., at least 360 degrees around the circumference of blood vessel 10) to provide greater vessel control. In another embodiment, the tip of clamp 50 may first be used to separate connective tissue (not shown) from blood vessel 10. For example, clamp 50, such as a Harken clamp or Sen dissector, may be maneuvered around the back of vessel 10 (which is attached to connective tissue) and the jaws of clamp 50 are repeatedly opened and closed in a technique known as "spreading." The clamp jaws are opened and closed with minimal force to minimize the risk of tearing major arteries and veins. An alternate technique that can reduce the probability of vessel 10 damage is to close the jaws of clamp 50 and position the tip 51 of clamp 50 around the back of vessel 10. Clamp 50 may be rotationally oscillated with respect to a central axis that extends along the length of clamp 50 and moved from side to side such that tip 51 oscillates and moves along the length of vessel 10. Sub-centimeter movement of clamp 50 along the length of vessel 10 allows clamp 50 to find the path of least resistance, thereby separating vessel 10 from surrounding connective tissue. This technique has far less mechanical advantage than the "spreading" technique and, hence, less risk of vessel 10 damage. Once vessel 10 has been separated from connective tissue, elongate flexible member 20 may be looped around vessel 10 and clamped directly with clamp 50. Vessel 10 may then be circumferentially dissected so that surgery may continue.

Once clamp 50 has been safely passed behind vessel 10, the act of grasping a free end of elongate flexible member 20, such as umbilical tape or surgical loop material, can cause soft tissue or vessel 10 itself to be pinched in the clamp jaws. In this instance, clamp 50 must be opened, thereby losing the free end of elongate flexible member 20 and a second attempt must be made. Accordingly, it is sometimes preferred to avoid the use of clamp so as the primary mechanism for separating vessel 10 from surrounding tissue.

Figure 3A:
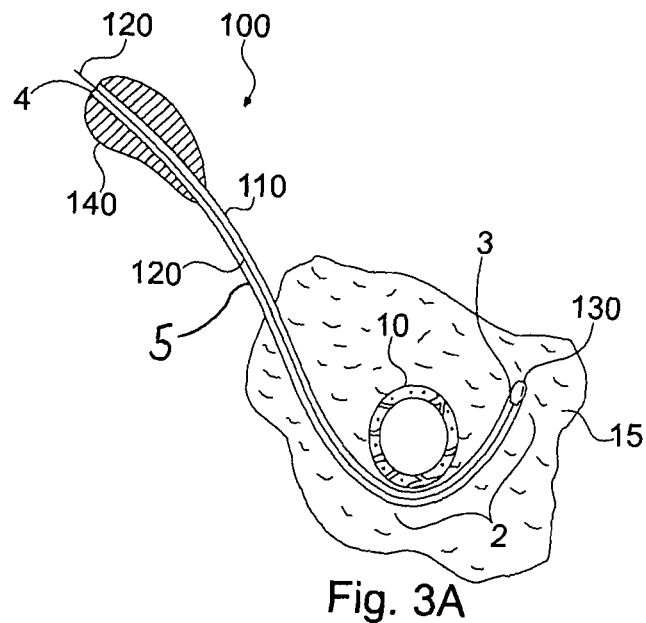
FIG. 3A is a schematic cross-sectional view of an exemplary embodiment of a device for facilitating access to a perimeter surface of a vessel according to aspects of the invention.

Referring now to FIG. 3A, according to an embodiment of the invention, a device 100 having an elongate body 110 is shown inserted behind blood vessel 10 and positioned adjacent the perimeter surface of vessel 10. Elongate body 110 contains an elongate flexible member 120 with an atraumatic tip 130 positioned at, and tethered (e.g., tied)to, a distal end of flexible member 120. Tip 130 is flexible and smoothly tapered with a blunt end such that the elongate body 110 and tip 130 assembly can be inserted behind blood vessel 10 with minimal or no damage to surrounding tissue 15 and blood vessel 10. As will be described in detail below, oscillating an atraumatic tip 130, such as a smooth "bullet" shaped tip 130 that is made of rubber or other pliable material, accommodates the resiliency of the blood vessel 10 so device 100 may be inserted underneath the blood vessel 10.

Elongate body 110 has a curved distal portion 2 and a distal end 3 that releasably engages atraumatic tip 130. Elongate body 110 also has a curved proximal portion 5 that is curved in an opposite direction to the curved distal portion 2. Elongate body 110 also has surface positioned to guide the elongate flexible member 120 such that flexible member 120 may be extracted longitudinally from the distal end 3 of elongate body 110. For example, tip 130 may be grasped and pulled from elongate body 110, thereby extracting flexible member 120 from elongate body 110. An ergonomic handle 140 is attached to elongate body 110 and is adapted to allow a surgeon to manipulate the device 100 behind blood vessel 10. One exemplary form of manipulation is slightly oscillating the tipped end of elongate body 110 from side to side, i.e., by rotating the handle 140 about the axis of elongate body 110, while maneuvering tip 130 further behind vessel 10.

Elongate body 110 may be made from a flexible material incorporating a stiffener such as a wire or the like. In this embodiment, elongate body 110 is adapted to be shaped by the surgeon before use. In a similar embodiment, elongate body 110 may be made from a material that can be shaped when heated and becomes rigid when cooled to room temperature. These embodiments allow surgeons to form custom shaped elongate bodies prior to operating on a patient. According to another embodiment, elongate body 110 may be formed of a rigid material and packaged in a kit. Materials include polymers such as polyethylene, polypropylene, high density thermoplastics, and other polymer derivatives. It is contemplated that other non-metallic or metallic materials may also be used. The kit may include device 100 and flexible member 120 so they may be disposable after surgery. For example, device 100 may be preloaded with atraumatic tip 130 and flexible member 120 such that the entire device 100 including the flexible member 120, tip 130, and elongate body 110 may be disposed after use.

In yet another embodiment, elongate body 110 may be formed in a variety of lengths, diameters, shapes, and sizes that are adapted to be used with flexible member 120 of various sizes or specific vessels to be secured or body structures to be manipulated. For example, an elongate body 110 having a large diameter can be used to accommodate a flexible member 120 having a large diameter (e.g., larger wire gauge), whereas an elongate body 110 having a smaller diameter may be used for thinner flexible members 120. In yet another embodiment, device 100 may be used for body structures other than blood vessels. For example, a body vessel that may be secured using device 100 is the esophagus. Device 100 may also be adapted for laparoscopic or thoracoscopic use. In minimally invasive spine surgery, for example, device 100 may be used to isolate the aorta so the tip 130 and attached flexible member 120 may be used to pull the aorta away from the spine. Accordingly, device 100 may have various shapes and sizes that can be adapted for particular areas of the anatomy and particular modes of entry and operating procedures.

Also, the elongate body 110 of the device 100 can be made steerable in a manner such as that utilized in guidewire or endoscopes or other manipulable instruments. A steerable elongate body 110 would permit the surgeon to change the curvature of the end portion so as to facilitate advancement of the device between a vessel and surrounding tissue.

Figure 3B:
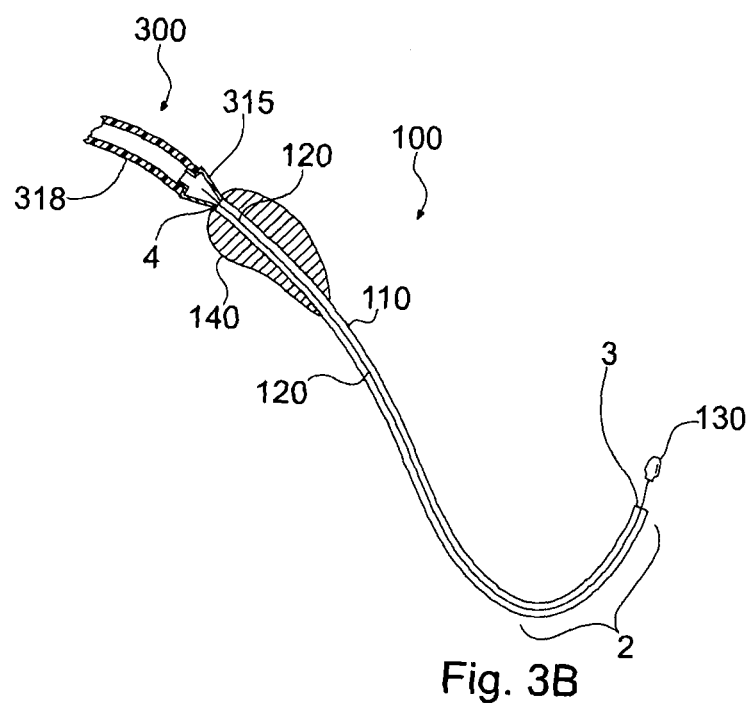
FIG. 3B is a schematic cross-sectional view of the device shown in FIG. 3A having a suctioning tip coupled to an end of the device to facilitate insertion of the flexible elongate member according to aspects of the invention.

Referring to FIG. 3B, according to an exemplary embodiment of the invention, a suctioning device 300 may be positioned at a proximal 4 or distal end 3 of elongate body 110 and provide a vacuum to facilitate insertion of the flexible member 120 into the elongate body 110. Aspects of the suctioning device 300 and methods of inserting flexible member 120 into elongate body 110 will be described in further detail below.

Figure 4:
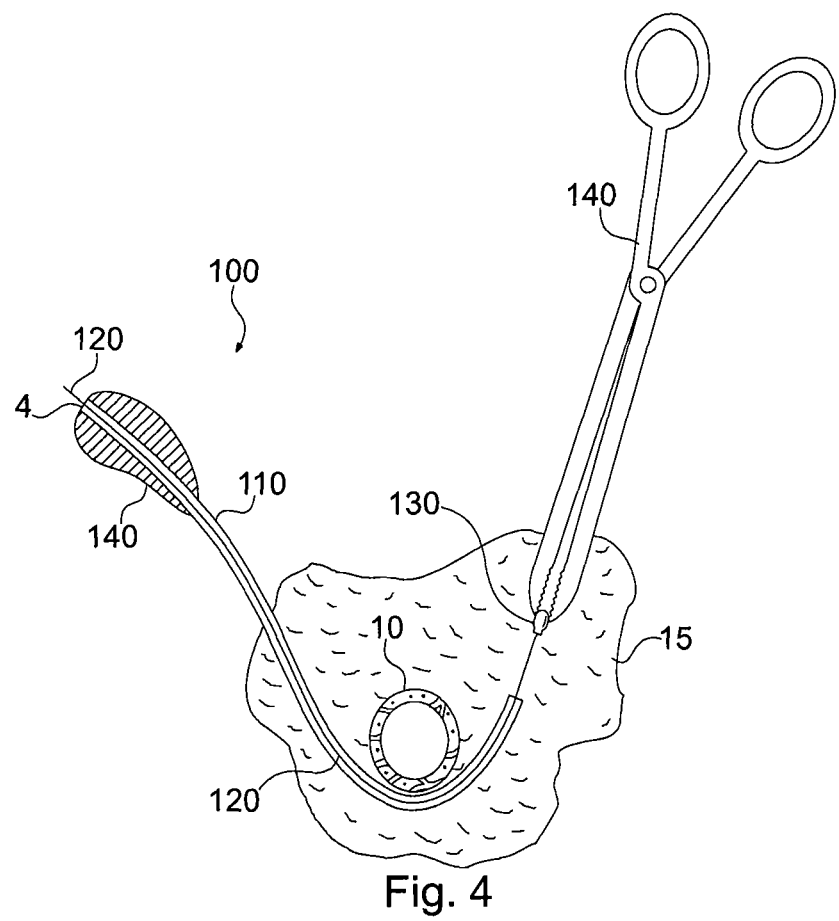
FIG. 4 is a schematic cross-sectional view of the device shown in FIG. 3 having an atraumatic tip grasped and pulled away from an elongate body of the device according to aspects of the invention.
Figure 5:
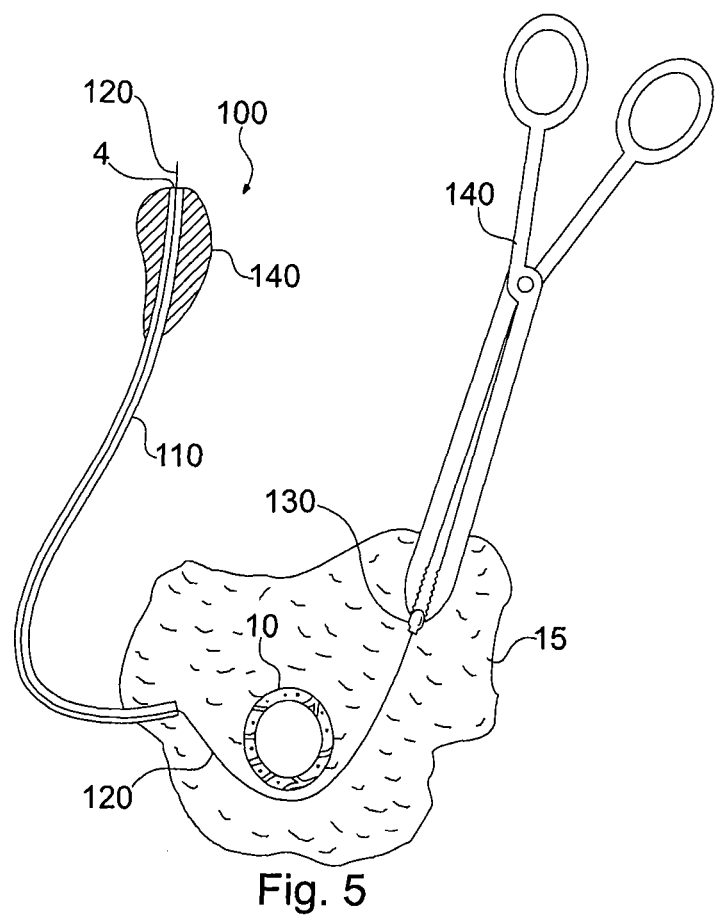
FIG. 5 is a schematic cross-sectional view of the device shown in FIGS. 3 and 4, according to aspects of the invention.

As shown in FIG. 4, once elongate body 110 and tip 130 assembly is positioned behind vessel 10, e.g., such that tip 130 is on an opposite side of vessel 10 from which tip 130 was first inserted, tip 130 may be grasped by a clamp 140 or other means such as hands or forceps, and pulled away from elongate body 110. As shown in FIG. 5, when tip 130 has been grasped, elongate body 110 can be partially or fully withdrawn from behind blood vessel 10, thereby leaving behind a length of elongate flexible member 120. Once flexible member 120 has encircled vessel 10, means for clamping flexible member 120, e.g., umbilical tape, suture, or cord, against vessel 10, are employed.

Figure 6:
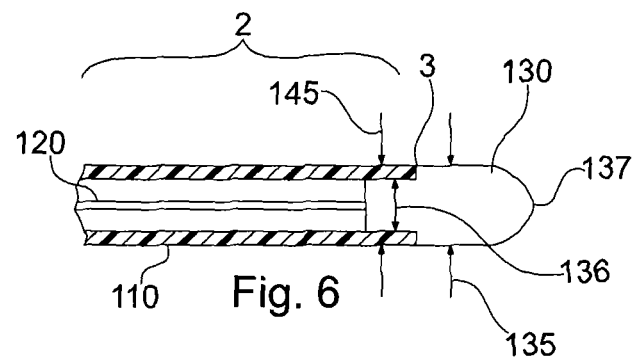
FIG. 6 is a schematic cross-sectional view of an exemplary embodiment of a distal portion of the device shown in FIGS. 3-5 according to aspects of the invention.

Referring now to FIG. 6, a distal portion 2 of elongate body 110 is illustrated with distal end 3 releasably engaging a portion of atraumatic tip 130. In an embodiment, distal portion 2 of elongate body 110 secures tip 130 when the device 100 is being inserted and oscillated as described herein. As shown in FIG. 6, the outside diameter 135 of tip 130 which is positioned and seated outside elongate body 110 is as wide as the outside diameter 145 of elongate body 110, so as to present a smooth surface where tip 130 and elongate body 110 meet. The portion of tip 130 that fits inside elongate body 110 is sized so that its outer diameter 136 allows tip 130 to fit snuggly into distal portion 2 of elongate body 110, while allowing tip 130 to be withdrawn when grasped. In one embodiment, elongate flexible member 120 is optionally pulled tight inside elongate body 110 to hold tip 130 in place until tip 130 has been manipulated around the back of vessel 10 and pulled away from distal end 3. According to another embodiment, tip 130 may be tapered from the outside diameter 145 of elongate body 110 to a blunt end 137. Tip 130 may also be made from rubber or silicon or any other suitable flexible material that is resilient and makes it easy to be grasp with a clamp or fingers or other instrument when extracting tip 130 from elongate body 110.

Figure 7:
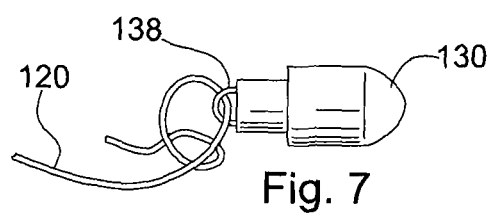
FIG. 7 is a schematic view of an exemplary embodiment of a device for impeding the flow of blood through a vessel according to aspects of the invention.
Figure 8:
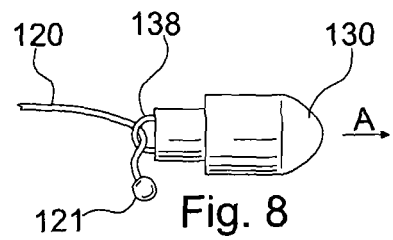
FIG. 8 is a schematic view of another exemplary embodiment of a device for impeding the flow of blood through a vessel according to aspects of the invention.
Figure 9:
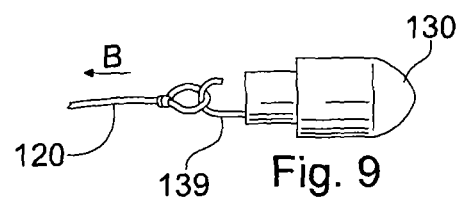
FIG. 9 is a schematic view of yet another exemplary embodiment of a device for impeding the flow of blood through a vessel according to aspects of the invention.

Referring now to FIGS. 7-9, various embodiments of a device for impeding the flow of blood through a vessel are illustrated. The device includes an atraumatic tip 130 and a flexible member 120. According to one embodiment shown in FIG. 7, a loop 138 is coupled to a distal end of tip 130. Flexible member 120 may be inserted through loop 138 to allow flexible member 120 to be secured to tip 130. In another embodiment, shown in FIG. 8, flexible member 120 having a bulbous end 121 may be inserted through loop 138. Bulbous end 121 is larger than the opening of loop 138 such that when tip 130 is pulled in a direction given by arrow A, flexible member 120 is also pulled in the same direction. In yet another embodiment, shown in FIG. 9, tip 130 has a hook 139 to catch the flexible member 120. Flexible member 120 may have a loop which is configured to couple to hook 139. According to an exemplary embodiment, hook 139 may have a V-shape or U-shape for attachment of the flexible member 120 loop onto tip 130. In other embodiments it is contemplated that flexible member 120 may not have a loop and other hook 139 shapes may also be used. Additionally, the surface of hook 139 may include serrations to assist frictional engagement of flexible member 120 onto hook 139.

In an exemplary embodiment, the loop of flexible member 120 is elastic and could be stretched onto hook 139. Once flexible member 120 is loaded through handle 140 and into elongate body 110 (FIG. 5), flexible member 120 may be tensioned in a direction shown by arrow B so the loop portion of the flexible member 120 is tightly secured onto hook 139.

According to yet another embodiment, flexible member 120 may be an umbilical tape that has a planar surface so it that may be easier to catch and attach a portion of the umbilical tape onto hook 139.

Referring to FIGS. 3B and 7-9, according to an embodiment of the invention, a tip 315 of a suctioning device 300 may be positioned at a proximal 4 or distal end 3 of elongate body 110 and provide a vacuum to facilitate insertion of the flexible member 120 into the elongate body 110. According to an exemplary embodiment, tip 315 may be a Yankauer tip that is coupled to a distal portion of tubing 318. The proximal portion of the tubing 318 may be coupled to a conventional suction source such as a wall outlet or portable device, thereby providing the suction to draw flexible member 120 from the distal end 3 of elongate body 110 into the lumen of device 100. It is contemplated that other suction tips 315 and tubing 318 may be used with device 100 to facilitate insertion of the flexible member 120 into the elongate body 110. Alternatively, device 100 may include a miniature ratcheting cleat attached to elongate body 110 to allow unidirectional passage of flexible member 120 into elongate body 110. For example, the ratcheting cleat may resemble a miniaturized ratchet, like those found on sailboats, that allow unidirectional passage of rope.

In yet another embodiment, flexible member 120 may be inserted into elongate body 110 using a wire loop like that used in sewing to introduce thread through the eye of a needle. For example, the wire loop may extend from a flexible plastic barrel and may be inserted through the proximal 4 or distal end 3 of elongate body 110. The wire loop may then be used to catch a portion of flexible member 110 that is inserted in elongate body 110 and withdrawn from elongate body 110, thereby facilitating passage of flexible member 110 through a proximal 4 or distal 3 end of elongate body 110. In this embodiment, the flexible plastic barrel may be prepackaged in a kit including device 100, flexible member 110, and an atraumatic tip 130.

Figure 10:
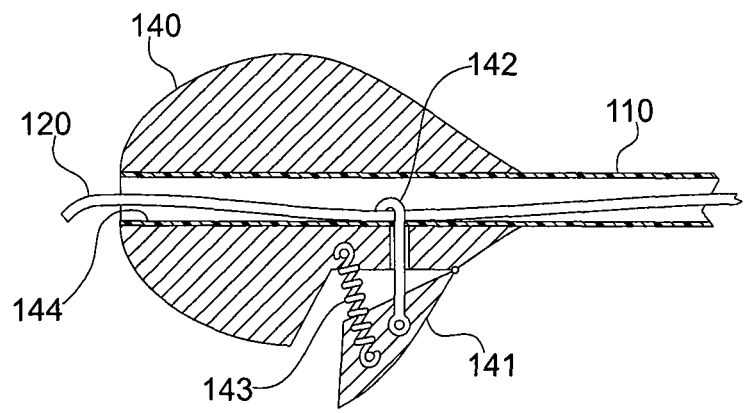
FIG. 10 is a schematic cross-sectional view of an exemplary embodiment of a handle and clamp assembly according to aspects of this invention.

Referring now to FIG. 10, in an exemplary embodiment, a proximal portion of elongate body 110 includes a releaseable clamp assembly for securing flexible member 120 to an inner surface 144 of elongate body 110. Thus, clamp assembly selectively prevents or inhibits the longitudinal movement of flexible member 120 from elongate body 110. At the handle portion 140 of elongate body 110, the clamp assembly includes a spring-loaded or otherwise biased trigger 141, which is connected to a hook or arm 142. Hook 142 fits inside an opening within elongate body 110 through which elongate flexible member 120 is positioned. Flexible member 120 is held snuggly against the inside surface 144 of elongate body 110 by the force of spring 143 or other bias means when trigger 141 is not depressed. When trigger 141 is depressed, hook 142 is moved away from the inside wall 144 and elongate flexible member 120 is released to permit relative movement of the member 120 with respect to the body 110. Thus, tip 130 (not shown in FIG. 10) may be pulled out of elongate body 110 along with a portion of flexible member 120.

Figure 11:
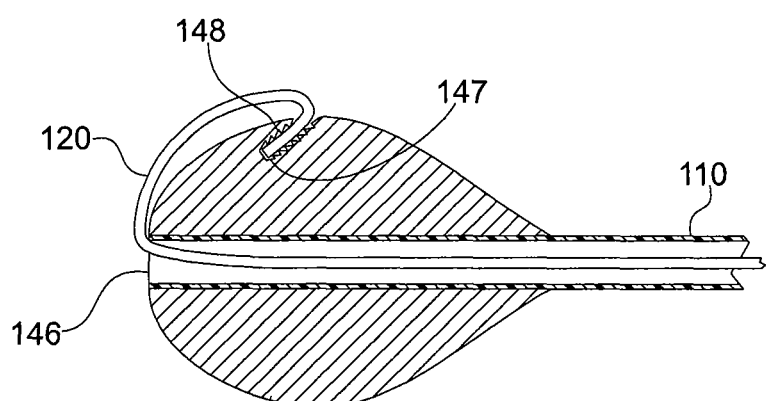
FIG. 11 is a schematic cross-sectional view of another exemplary embodiment of a handle having a cleat according to aspects of this invention.

In another embodiment, shown in FIG. 11, flexible member 120 exits an opening 146 of elongate body 110 and is secured by wrapping a portion of flexible member 120 around a cleat 147 or similar engaging means formed in handle 140. Cleat 147 may have groves/ridges 148 to secure the portion of flexible member 120 to handle 140.

Figure 12:
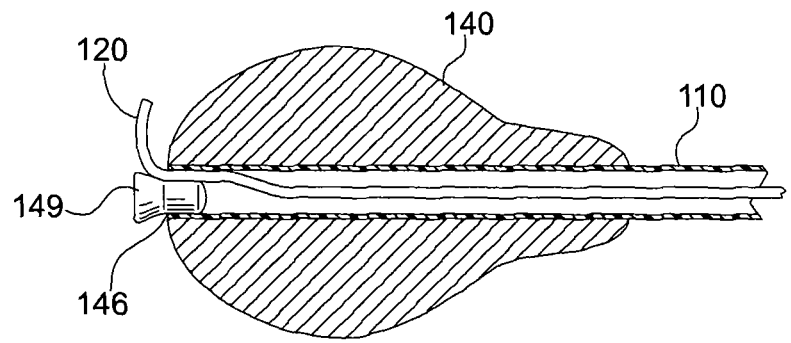
FIG. 12 is a schematic cross-sectional view of yet another exemplary embodiment of a handle having a plug according to aspects of this invention.

In yet another embodiment, shown in FIG. 12, after flexible member 120 is pulled tight within elongate body 110, elongate flexible member 120 may be secured in place with a plug 149 which is inserted into opening 146 of elongate body 110. When plug 149 is removed, tip 130 (not shown) at an opposite end of opening 146 may be grasped and pulled to release flexible member 120.

Figure 13:
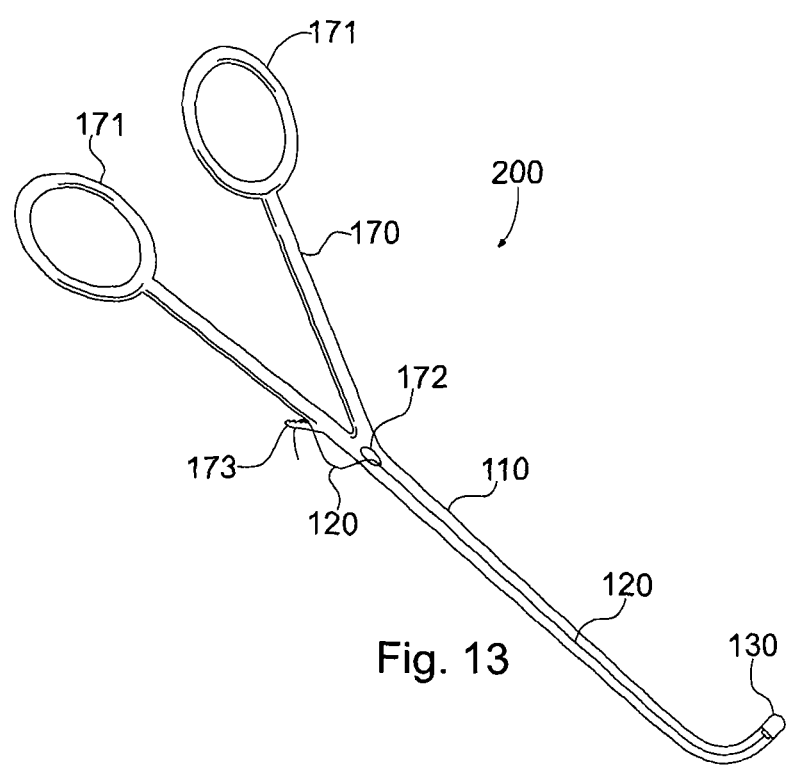
FIG. 13 is a schematic cross-sectional view of another exemplary embodiment of a surgical device according to an aspect of this invention.

Referring now to FIG. 13, in a further embodiment elongate body 110 is attached to, or forms a part of, a handle 170 comprising two loops 171 adapted to be held with a user's fingers. The loops 171 are such as those that may be found on a surgical clamp. The device 200 can include an exit hole 172 for flexible member 120 and a cleat 173 for securing flexible member 120, such as that illustrated in FIG. 11. This embodiment allows surgeons who are familiar with the technique of using a surgical clamp to insert a vascular tape to perform the same manipulations without having to retrain for new physical movements. While FIG. 13 shows the curve of elongate body 110 being in the same plane as the cross-sectional drawing, the curve of the elongate body 110 can be in any position relative to the plane in which the two loops 171 lie or may be manipulable or steerable by the surgeon. For example, the lower portion of elongate body 110 can be rotated with respect to the plane of the two finger loops 171 and secured in position, thus making it possible for orienting the curved portion in a variety of positions.

Although the invention has been described primarily in connection with embodiments configured for the manipulation of blood vessels, it is contemplated that the apparatus and method provided by this invention applies to any control or manipulation of any body structure. Accordingly, this invention is not limited to the manipulation of blood vessels.

While the invention has been described in detail and with reference to specific examples thereof, it will be apparent to one skilled in the art that various changes and modifications can be made therein without departing from the spirit and scope thereof.

What is claimed:

1. A device for facilitating access to a perimeter surface of a body structure comprising:
    an elongate flexible member configured to be positioned adjacent the perimeter surface of the body structure;
    an atraumatic tip positioned at a distal end of the elongate flexible member and having a width greater than that of the flexible member;
    an elongate body having a surface positioned to guide the elongate flexible member and to permit longitudinal movement of the flexible member with respect to the elongate body, wherein the elongate flexible member extends within the elongate body of the device, the body having a curved distal portion and a distal end releasably engaging the atraumatic tip;
    a handle coupled to the elongate body, wherein the elongate body extends at least partially within the handle;
    a depressible trigger that is moveably positioned with respect to the handle; and
    a hook connected to the trigger and positioned within an opening that is defined within the elongate body,
    wherein, when the trigger is depressed, the hook is spaced from an inside surface of the elongate body and the elongate flexible member is released to permit relative movement of the elongate flexible member with respect to the elongate body, and, when the trigger is not depressed, the elongate flexible member is held against the inside surface of the elongate body by the hook to either prevent or limit relative movement of the elongate flexible member with respect to the elongate body.

2. The device of claim 1, wherein the elongate body comprises a tubular structure, and the surface of the elongate body includes an inner surface of the tubular structure.

3. The device of claim 1, wherein the elongate body comprises a flexible material.

4. The device of claim 1, wherein the elongate body comprises a rigid material.

5. The device of claim 1, wherein the tip is coupled to the flexible member.

6. The device of claim 5, wherein the tip is tethered to the flexible member.

7. The device of claim 5, wherein the elongate body has a curved proximal portion that is curved in an opposite direction to the curve of the curved distal portion.

8. The device of claim 1, wherein the distal portion of the tip has a width equivalent to that of the elongate body.

9. The device of claim 1, wherein the tip is a flexible material.

10. The device of claim 1, wherein the tip has a blunted end.

\* \* \* \* \*